United States Patent [19]

Schrider

[11] 4,053,631
[45] Oct. 11, 1977

[54] SYSTEMIC CONTROL OF ECTOPARASITES WITH α-CYANO-M-PHENOXYBENZYL α-$C_1$-$C_4$ ALKYL-2-NAPHTHALENEACETATES

[75] Inventor: Michael Stanley Schrider, South Bound Brook, N.J.

[73] Assignee: American Cyanamid Company, Stamford, Conn.

[21] Appl. No.: 673,246

[22] Filed: Apr. 2, 1976

[51] Int. Cl.$^2$ .......................................... A61K 31/275
[52] U.S. Cl. .............................. 424/304; 424/DIG. 8
[58] Field of Search .......................... 424/304, DIG. 8

[56] References Cited

U.S. PATENT DOCUMENTS

| 3,835,176 | 9/1974 | Matsuo et al. ...................... 424/304 |
| 3,962,458 | 6/1976 | Schrider .............................. 424/304 |

*Primary Examiner*—V. D. Turner
*Attorney, Agent, or Firm*—H. G. Jackson

[57] ABSTRACT

The invention is the use of α-cyano-m-phenoxybenzyl $C_1$-$C_4$ alkyl-2-naphthaleneacetates as systemic insecticidal and acaricidal agents for treatment of homothermic animals.

10 Claims, No Drawings

SYSTEMIC CONTROL OF ECTOPARASITES WITH α-CYANO-M-PHENOXYBENZYL α-$C_1$-$C_4$ ALKYL-2-NAPHTHALENEACETATES

CROSS REFERENCE TO RELATED APPLICATIONS

The co-pending Application Ser. No. 673,244, of Roger Williams Addor and Venkataraman Kameswaran, filed of even date discloses the compounds useful in my invention.

BACKGROUND OF THE INVENTION

1. Field of the Invention

The field of the invention is systemic control of ectoparasites with α-cyano-m-phenoxybenzyl-α-$C_1$-$C_4$-alkyl-2-naphthaleneacetates.

2. The Prior art

I am not familiar with any art, other than the application of R. W. Addor et al. referred to above and made of reference herein, that describes the compound of this invention for any use whatsoever. The closest art of which I am aware, is the pyrethroid art which decribes chemical compounds that contain the α-cyano-m-phenoxybenzyl substituents and are shown to possess insecticidal properties. My invention provides a process wherein α-cyano-m-phenoxybenzyl α-$C_1$-$C_4$-alkyl-2-naphthaleneacetates are highly effective systemic insecticidal and acaricidal agents useful for the treatment of warm-blooded or homothermic animals. U.S. Pat. No. 3,835,176, issued Sept. 10, 1974 and assigned to Sumitomo Chemical Company Limited of Japan discloses alpha-cyanobenzylcyclopropanecarboxylates containing a m-phenoxy substituent, as insecticidal agents. There is, however, no disclosure of animal systemic insecticidal or acaricidal properties for the patentees compounds and the compounds are chemically distinct from those of the subject application.

SUMMARY OF THE INVENTION

The invention is a method for the systemic control of ectoparasites, particularly insects and acarina which parasitize homothermic animals which comprises admininstering to the animals a systemically effective amount against the pests of an α-cyano-m-phenoxybenzyl α-$C_1$-$C_4$-alkyl-2-naphthaleneacetate of the formula:

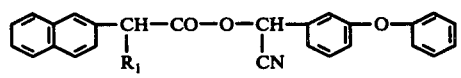

(I)

wherein $R_1$ is alkyl $C_1$-$C_4$.

DETAILED DESCRIPTION

The phenoxybenzyl-α-alkyl-2-naphthaleneacetates represented by formula I above, can be prepared by reaction of approximately equimolar amounts of a 2-naphthylacetyl halide (II) preferably the chloride, and a benzyl alcohol (III). The reaction is generally conducted in the presence of a hydrocarbon or halocarbon solvent such as heptane, toluene, xylene, ethylene chloride or the like, at a temperature between about 0° C and 30° C, and preferably in the presence of an acid acceptor such as pyridine, triethylamine, or aqueous sodium hydroxide.

Using pyridine as representative of the acid acceptor, the reaction may be illustrated as follows:

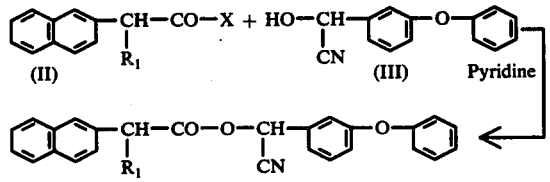

wherein $R_1$ is alkyl $C_1$-$C_4$ and X is halogen such as chloro or bromo.

The formula (II) naphthaleneacetyl halide can be obtained by reaction of the appropriate alkylated-2-naphthaleneacetic acid with a thionyl halide such as thionyl chloride or thionyl bromide, or a phosphorus halide such as phosphorus trichloride, phosphorus tribromide or phosphorus pentachloride in the presence of an organic solvent such as toluene, methylene chloride, benzene or a benzene hexane mixture. The halide and the acid are employed in approximately equimolar amounts, although as much as two mole equivalents of the halide per mole of acid may be used, and the reaction is preferably conducted at about the refluxing temperature of the solvent, generally between about 40° C and 110° C. This reaction may be graphically illustrated as follows:

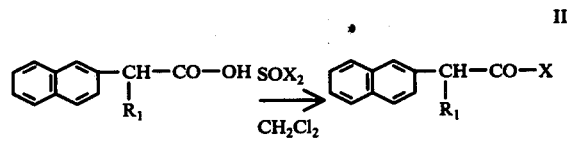

II wherein $R_1$ and X are as previously described.

The alkylated-2-naphthaleneacetic acid, employed in the above-illustrated reaction, can be prepared from the commercially available 2-naphthaleneacetonitrile. The process involves reacting approximately equimolar amounts of 2-naphthaleneacetonitrile and an alkyl halide represented by the formula: $R_1X$, wherein $R_1$ is alkyl $C_1$-$C_4$ as defined above and X is halogen, such as chloro, iodo or bromo. An excess of the alkyl halide may, of course, be used. This reaction is conducted in the presence of a base and ammonia an aprotic solvent such as toluene, xylene, diethylether or the like. The reaction yields the corresponding alkylated-2-naphthaleneacetonitrile which is then readily hydrolyzed to the alkylated-2-naphthaleneacetic acid. This reaction is conducted with a strong mineral acid and water at an elevated temperature, preferably a temperature between 120° C and 150° C. The reactions can be graphically illustrated as follows:

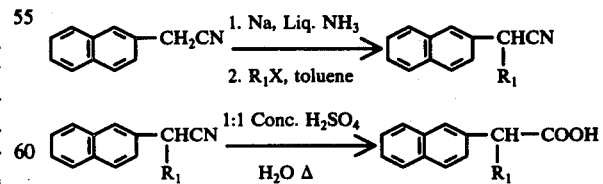

wherein $R_1$ and X are as described above.

The preparation of α-tert-butyl-2-naphthaleneacetonitrile is carried out using 2-naphthaldehyde by the following sequence of reactions (1) reaction with t-butyl magnesium chloride, (2) conversion of the neopentyl alcohol to the chloride using thionyl chloride, (3) preparation of the Grignard reagent with magnesium in tetrahydrofuran, and, (4) carboxylation with carbon dioxide.

Typical aprotic solvents which can be employed in the alkylation of 2-naphthaleneacetonitrile include, toluene, xylenes, benzene, methylcyclohexane, dimethoxyethane and the like.

The above alkylation can be conducted using commercially available sodium amide or an alkali amide prepared in situ from sodium or potassium metal in liquid ammonia. Following removal of excess ammonia, the alkylation proceeds in the presence of an aprotic solvent preferably at a temperature between 50° C and 120° C.

An alternate route to the alkylation of 2-naphthaleneacetonitrile and one which is preferred in large-scale reactions is to use $R_1X$ as the alkylating agent in the presence of aqueous alkali, e.g. 50% aqueous sodium hydroxide, as the base. The reaction is promoted by phase-transfer catalysts, such catalysts being of the quaternary ammonium or quaternary phosphonium salt or crown ether types. Suitable quaternary ammonium or phosphonium salts include benzyltriethylammonium chloride, tetrabutylammonium hydrogen sulfate, cetyltrimethylammonium chloride, tricaprylmethylammonium chloride, hexadecyltributylphosphonium bromide, and the like. These salts may be incorporated to the extent of about 0.5 to 100 mole percent based on the moles of starting acetonitrile used. Suitable crown ethers include 18-crown-6, dibenzo-18-crown-6, and dicyclohexyl-18-crown-6. Crown ethers are used in the range of 0.5 to 5 mole percent based on the moles of alkylating agent used.

Typical acids which can be employed in the conversion of the alkylated-2-naphthaleneacetonitrile to the corresponding acid, are sulfuric acid, hydrochloric acid, phosphoric acid, and mixtures thereof. For the conversion, the presence of water in the reaction mixture is essential and it has been found that the reaction appears to proceed satisfactorily only at elevated temperatures and preferably between 120° C and 150° C. Somewhat higher or lower temperatures may be used, but excessive temperatures causing charring of the reaction mixture and at low temperatures the reaction does not proceed at an acceptable rate.

Further examples of the preparation of compounds useful in my invention are disclosed in the co-pending application of R. W. Addor et al. cross-referenced above, compounds useful in this invention include the following:

α-cyano-m-phenoxybenzyl α-n-butyl-2-naphthaleneacetate;
α-cyano-m-phenoxybenzyl α-t-butyl-2-naphthaleneacetate;
α-cyano-m-phenoxybenzyl α-ethyl-2-naphthaleneacetate;
α-cyano-m-phenoxybenzyl α-n-propyl-2-naphthaleneacetate;
α-cyano-m-phenoxybenzyl α-sec-butyl-2-naphthaleneacetate;
α-cyano-m-phenoxybenzyl α-isobutyl-2-naphthaleneacetate;
α-cyano-m-phenoxybenzyl α-methyl-2-naphthaleneacetate;
α-cyano-m-phenoxybenzyl α-isopropyl-2-naphthaleneacetate.

The compounds can be administered to the animal host orally, topically or parenterally, for use as animal systemic insecticidal and acaricidal agents. When given orally, it may be in any convenient form designed for oral administration such as a bolus, capsule, tablet or as an oral drench. The active agent may also be incorporated in an edible animal feedstuff such as a nutritionally balanced diet containing from 0.001% to 3.0%, and preferably 0.001% to 1.5% by weight of feed of the active compound.

When the active compound is administered as a single oral dose, generally about 25 mg to 1000 mg of compound per kg of animal body weight, and preferably 100 to 500 mg of compound per kg of animal body weight is used.

If desired, the systemic insecticidal and acaricidial agent may be introduced into the body of the animal by subcutaneous, intramuscular or intraperitioneal injection, such that it may be distributed through the animal's body by the action of the animal's circulatory system. In practice, the systemic agent may be dissolved or dispersed in a pharmaceutically acceptable carrier such as water, propylene glycol, vegetable oil, glycerol formal, or the like, for administration.

For systemic control of insects and acarina which attack homothermic animals, the active α-cyano-m-phenoxybenzyl α-$C_1$-$C_4$-alkyl-2-naphthaleneacetate may also be administered to the animal in the form of a pour-on formulation. Such formulation is applied generally to the back of the animal such that the active ingredient is permitted to come in contact with the animals skin. The active ingredient penetrates through the skin, is picked up by the body fluids and is circulated through the animals body affording it the protection of the active ingredient.

Pour-on formulations generally contain from about 7% to about 35% and preferably 10% to 15% by weight of the active ingredient dispersed in a diluent composition comprising a vegetable oil, aromatic solvent and a ketone. A typical formulation which is useful in the practice of the present invention is as follows: α-cyano-m-phenoxybenzyl α-$C_1$-$C_4$-alkyl-2-naphthaleneacetate 13% by weight, 25% by weight of cyclohexanone, 46% by weight of xylene and 16% by weight of corn oil.

Surprisingly, it has been found that in addition to the systemic control of ectoparasites which attack warm-blooded animals, administering the α-cyano-m-phenoxybenzyl α-$C_1$-$C_4$ alkyl-2-naphthaleneacetate to homothermic animals has the advantage that a portion of the active material passes through the treated animal and controls fly larvae feeding in the manure eliminated by the treated animal.

Advantageously, the systemic agents of this invention have relatively low mammalian toxicity and are effective for protecting a variety of animals, particularly livestock and domestic animals such as cattle, sheep, horses, dogs, cats, zoo and laboratory animals and the like, from attack by fleas, mosquitoes, flies, ticks, and the like.

The invention is further demonstrated by the examples provided below.

EXAMPLE 1

Systemic Control of Stable Flies on Mice

To determine the effectiveness of the compounds of the present invention as animal systemic insecticidal agents, test compounds are mixed in 10% acetone-90% sesame oil and administered orally (by gavage) to two 20 g Swiss-Webster white female mice at 100 and 400 mg/kg. Mice are dosed with 10% acetone/90% corn oil and used as a controls.

One hour after treatment, 10 stable flies (*Stomoxys calcitrans*) are placed in a cage with each mouse and allowed 18 hours to feed. Mortality counts are made at 24 hours and data obtained are reported in the table below.

Table I

| Compound | Systemic Insecticidal Activity of Test Compounds | | | |
|---|---|---|---|---|
| | Dose mg/kg | No. Mice Treated | No. Flies/Mouse | % Mortality of Flies Feeding on Treated Mice |
| α-Cyano-m-phenoxybenzyl α-methyl-2-naphthaleneacetate | 400 | 3 | 10 | 73 |
| | 100 | 3 | 10 | 33 |
| α-Cyano-m-phenoxybenzyl α-sec-butyl-2-naphthaleacetate | 400 | 3 | 10 | 100 |
| | 100 | 3 | 10 | 13 |
| α-Cyano-m-phenoxybenzyl α-iso-butyl-2-naphthaleneacetate | 400 | 3 | 10 | 26 |
| | 100 | 3 | 10 | 0 |
| α-Cyano-m-phenoxybenzyl α-ethyl-2-naphthaleneacetate | 400 | 3 | 10 | 100 |
| | 100 | 3 | 10 | 13 |
| Control | — | 3 | 10 | 3 |

EXAMPLE 2

The systemic activity of α-cyano-m-phenoxybenzyl α-isopropyl-2-naphthaleneacetate is determined using the procedure of Example 1, excepting that 25, 100 and 400 mg of compound per kg of animal body weight is used. In one test 100 and 400 mg/kg of test compound is evaluated against controls and in a second test 25 and 100 mg/kg of test compound is evaluated. Results are reported in Table II below.

Table II

| Compound | Systemic Insecticidal Activity of Test Compounds | | | |
|---|---|---|---|---|
| | Dose mg/kg | No. Mice Treated | No. Flies/Mouse | % Mortality of Flies Feeding on Treated Mice |
| α-Cyano-m-phenoxybenzyl α-iso-propyl-2-naphthaleneacetate | 400 | 4 | 10 | 100 |
| | 100 | 4 | 10 | 85 |
| Control | — | 4 | 10 | 17 |
| α-Cyano-m-phenoxybenzyl α-iso-propyl-2-naphthaleneacetate | 100 | 3 | 10 | 100 |
| | 25 | 3 | 10 | 93 |
| Control | — | 3 | 10 | 0 |

I claim:

1. A method for the systemic control of ectoparasites which attack warm-blooded animals, comprising administering to the warm-blooded animals a systemically effective amount against the ectoparasites of a compound having a formula:

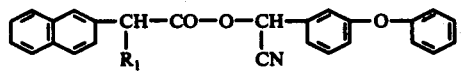

wherein $R_1$ is alkyl $C_1$-$C_4$.

2. A method according to claim 1, wherein the compound is administered, orally or parenterally, to the animal host at a dose level of from 25 mg/kg of animal body weight to about 1000 mg/kg of animal body weight.

3. A method according to claim 2 wherein the compound is α-cyano-m-phenoxybenzyl α-isopropyl-2-naphthaleneacetate.

4. A method according to claim 2 wherein the compound is α-cyano-m-phenoxybenzyl α-ethyl-2-naphthaleneacetate.

5. A method according to claim 2 wherein the compound is α-cyano-m-phenoxybenzyl α-methyl-2-naphthaleneacetate.

6. A method according to claim 2 wherein the compound is α-cyano-m-phenoxybenzyl α-isobutyl-2-naphthaleneacetate.

7. A method according to claim 2 wherein the compound is α-cyano-m-phenoxybenzyl α-sec-butyl-2-naphthaleneacetate.

8. A method according to claim 1 wherein the compound is administered in a nutritionally balanced animal feed containing from 0.001% to 3.0% of the α-cyano-m-phenoxybenzyl α-$C_1$-$C_4$-alkyl-2-naphthaleneacetate.

9. A method according to claim 1 wherein the compound is administered as a topical pour-on formulation containing from about 7% to 35% by weight of the α-cyano-m-phenoxybenzyl α-$C_1$-$C_4$-alkyl-2-naphthaleneacetate.

10. A method for treating animals to control fly larvae feeding in the eliminated manure therefrom comprising, orally administering to the animals from about 0.1 mg/kg of animal body weight to about 100 mg/kg of animal body weight of an α-cyano-m-phenoxybenzyl α-$C_1$-$C_4$-alkyl-2-naphthaleneacetate or an animal feed containing from 0.001% by weight to 3.0% by weight of the α-cyano-m-phenoxybenzyl α-$C_1$-$C_4$-2-naphthaleneacetate.

* * * * *